United States Patent [19]

Miller

[11] 4,309,382

[45] Jan. 5, 1982

[54] MOTOR VEHICLE DEODORIZING METHOD

[75] Inventor: Richard A. Miller, St. Louis, Mo.

[73] Assignee: Stewart Sanitary Supply, Inc., St. Louis, Mo.

[21] Appl. No.: 134,530

[22] Filed: Mar. 27, 1980

[51] Int. Cl.³ .......................... A61L 9/04; A61L 9/02; A61L 9/14
[52] U.S. Cl. ........................................ 422/4; 98/2.11; 134/6; 252/70; 252/170; 252/174.11; 252/DIG. 10; 422/5; 422/124
[58] Field of Search .................. 422/4, 5, 124; 134/6; 98/2.11; 252/70, 170, 174.11, DIG. 10

[56] References Cited

U.S. PATENT DOCUMENTS 3,259,050 7/1966 Grimm ................................ 98/2.11

FOREIGN PATENT DOCUMENTS 714019 7/1965 Canada ...................... 252/DIG. 10

Primary Examiner—Barry Richman
Attorney, Agent, or Firm—Polster, Polster & Lucchesi

[57] ABSTRACT

A solvent-evaporation type of deodorant is added to the windshield washer fluid reservoir of a motor vehicle. When the material is sprayed onto the windshield of the vehicle while the vehicle's air conditioning (heating, cooling or ventilating) system is running, the deodorant is drawn into the vehicle passenger compartment where it dissolves odor-causing particles and removes them.

3 Claims, 2 Drawing Figures

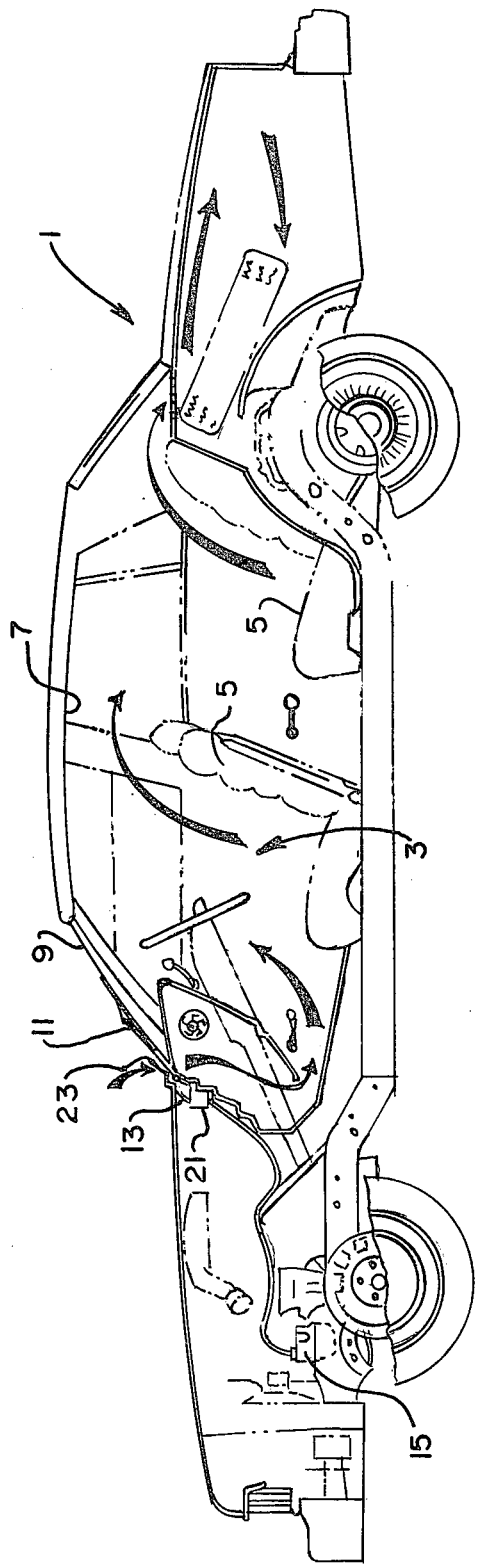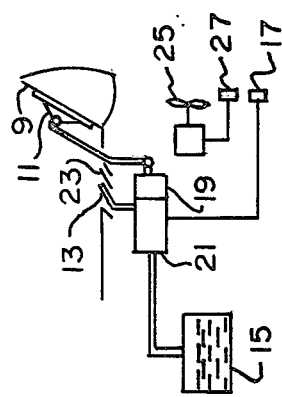

MOTOR VEHICLE DEODORIZING METHOD

BACKGROUND OF THE INVENTION

This invention relates to a system for removing odors from motor vehicles.

The problem of controlling odors in motor vehicles is roughly as old as the enclosed passenger compartment. Odors drawn into the passenger compartment from outside are sometimes objectionable. As often, the odors are the result of activities within the automobile, particularly smoking. In modern vehicles, smoke tends to collect in the top liner of the vehicle.

Attempts to remove odors from automobiles, particularly after the odor-causing particles have become lodged in the top liner or other upholstery, have met with only limited success. Materials which merely mask the odor with their own scent are generally objectionable and of limited use. Materials, such as active oxidants, which chemically react with odor-causing particles require treatment of the car when passengers are not in it, are frequently deleterious to some parts of the vehicle, and are not always effective. Recently, solvent-evaporation materials have been used with considerable success in removing serious odors from vehicles. The solvent-evaporation systems include an active ingredient which acts as a highly efficient solvent for most odor-causing particles, and which is capable of evaporation with the odor-causing particles in solution. If the vapor bearing the particles is swept from the passenger compartment before it condenses on a surface in the vehicle, the odor-causing particles, hence the odor, are swept away. The solvent evaporation materials are sprayed into the automobile, particularly around the top liner, the windows of the vehicle are opened, and a large fan is placed in the open trunk of the automobile to draw the vaporized particles out of the passenger compartment. Although this method is effective, it is also time consuming and cumbersome.

SUMMARY OF THE INVENTION

One of the objects of this invention is to provide an effective odor removing system for motor vehicles.

Another object is to provide such a system which is simple to use, requires no modification of the vehicle, and may be used selectively while the vehicle is occupied and in operation.

Other objects will become apparent in light of the following description and accompanying drawing.

In accordance with this invention, generally stated, a method is provided for deodorizing a motor vehicle of the conventional type which includes a passenger compartment, a windshield for the passenger compartment, windshield wipers for cleaning the windshield, a spray system for spraying a cleaning solvent onto the windshield, the spray system including a spray nozzle adapted to spray a solvent onto the windshield, a fluid reservoir for holding a solvent, and pump means for forcing solvent from the reservoir through the nozzle and onto the windshield for spreading across the windshield by the wipers, and an air conditioning system for the passenger compartment, the air conditioning system including an air intake generally adjacent the lower edge of the windshield, a fan for drawing air through the intake and into the passenger compartment, and outlet means for permitting a substantial quantity of air to escape the passenger compartment and the vehicle. The method comprises a step of adding to the fluid reservoir an operative quantity of a solvent-evaporation type of deodorant and a step of activating the air conditioning system and the windshield spray system to draw sufficient of the solvent-evaporation deodorant into the passenger compartment to evaporate odorant particles in the passenger compartment and evacuate the particles through the outlet.

The solvent-evaporation type of deodorant preferably comprises as its primary ingredient a three- to five-carbon alcohol, most preferably dimethyl carbinol. Preferably, the alcohol is present in the reservoir in a concentration of from ten percent to fifty percent by volume. Because the alcohol of the solvent-evaporation deodorant is not a particularly good glass cleaner, the reservoir also preferably also contains a substantial quantity of methanol and a quantity of detergent, the conventional components of windshield washing solutions. Dimethyl Carbinol and other three- to five-carbon alcohols have the virtue of being compatible with the methanol or glycol solvents typically employed in windshield washing solutions.

BRIEF DESCRIPTION OF THE DRAWING

FIG. 1 is a schematic view, partially cut away, of an automobile incorporating an odor removing system of the present invention.

FIG. 2 is a schematic drawing showing the parts of the automobile used in the process of the invention.

DESCRIPTION OF THE PREFERRED EMBODIMENT

Referring now to the drawings, reference numeral 1 indicates an automobile having a passenger compartment 3 including seats 5 and top liner 7. The automobile 1 is equipped with a conventional windshield 9, windshield wipers 11, windshield spray nozzles 13 and a windshield washer fluid reservoir 15. Activation of a switch 17 in the passenger compartment in the automobile activates a windshield wiper motor 19 and a pump 21 which sprays a measured amount of solution in the reservoir 15 through the nozzles 13 onto the windshield 9, where it is spread across the windshield by wipers 11 and cleans the windshield. Typically, the windshield washer fluid is a mixture of methanol, detergent and water, with a dye added. This system is conventional in present-day automobiles.

The automobile 1 also conventionally includes a ventilation system including an air intake 23 located at the base of the windshield 9. As indicated by arrows in FIG. 1, air is drawn from the outside through the air intake 23 by a fan 25 activated by a switch 27. The switch 27 may also include controls for a cooling or heating system. The ventilation, heating and cooling systems are known generically as air conditioning systems.

In accordance with the present invention, a solvent-evaporation type deodorant is added to the windshield washer reservoir 15. The quantity of solvent-evaporation deodorizer added is preferably about equal to the amount of windshield washer solution in the reservoir 15. If the solvent-evaporation deodorant contains about fifty percent dimethyl carbinol as the active ingredient, the active ingredient thereof constitutes about 25% of the total volume of liquid in the reservoir. Preferably, the deodorizer further includes a small amount of masking agent or perfume to mask the odor of the dimethyl carbinol as well as the objectionable odors within the passenger compartment, while the odors are being removed from the passenger compartment. Suitable masking agents are well known in the art.

To remove odors from the passenger compartment while the vehicle is in operation, the air conditioning system is turned on and the windshield washer switch 17 is activated. The solvent-evaporation deodorant is sprayed onto the windshield, where it evaporates. The vapor is drawn into the passenger compartment by the air conditioning system, as indicated by arrows in FIG. 1. It has been found that the movement of air within the passenger compartment is gentle enough to allow the vapors to partially condense and dissolve odor-causing particles in the upholstery and top liner of the vehicle, as well as dissolving particles in the air in the passenger compartment. Many modern vehicles have "flow-through" ventilation systems which constantly change the air in the passenger compartment. Other vehicles require sufficient means for air within the passenger compartment to escape, such as may easily be provided by cracking the windows open as shown in FIG. 1. Odors within the passenger compartment are quickly and effectively removed by this method.

Numerous variations in the odor removal system of the present invention, within the scope of the appended claims, will occur to those skilled in the art. Merely by way of example, the amount of the active solvent-evaporation ingredient may be varied from about 5% to nearly 100% of the contents of the fluid reservoir, although at the lower ranges the amount of active ingredient drawn into the vehicle is insufficient for major odors and at the upper ranges the windshield cleaning ability of the solution is impaired. Therefore, the preferred range of concentration is from about 10% to about 50% by volume. The active ingredient may be any liquid which is capable of dissolving or otherwise vaporizing odor-causing particles, although dimethyl carbinol is greatly preferred. These variations are merely illustrative.

I claim:

1. A method for deodorizing a motor vehicle, said motor vehicle including:
    a passenger compartment,
    a windshield for said passenger compartment,
    windshield wipers for cleaning said windshield,
    a spray system for spraying a cleaning solvent onto said windshield, said spray system including a spray nozzle adapted to spray a solvent onto said windshield, a fluid reservoir for holding a solvent, and pump means for forcing solvent from said reservoir through said nozzle and onto said windshield for spreading across said windshield by said wipers,
    an air conditioning system for said passenger compartment, said air conditioning system including an air intake generally adjacent the lower edge of said windshield, a fan for drawing air through said intake and into said passenger compartment, and outlet means for permitting a substantial quantity of air to escape said passenger compartment and said vehicle,
    said method comprising a step of adding to said fluid reservoir and operative quantity of a solvent-evaporation type of deodorant and a step of activating said air conditioning system and said windshield spray system to draw sufficient of said solvent-evaporation deodorant into said passenger compartment to evaporate odorant particles in said passenger compartment and evacuate said particles through said outlet, said solvent-evaporation type of deodorant comprising as its primary active ingredient a three to five carbon alcohol and further comprising a masking agent for masking objectionable odors present in said passenger compartment, said reservoir also containing methanol and a detergent.

2. The method of claim 1 wherein said three to five carbon alcohol is present in said reservoir in a concentration of from ten percent to fifty percent by volume.

3. The method of claim 2 wherein said alcohol is dimethyl carbinol.

* * * * *